(12) United States Patent
Yaegashi et al.

(10) Patent No.: US 7,943,802 B2
(45) Date of Patent: May 17, 2011

(54) NANOPARTICLE COMPOSITE

(75) Inventors: Hideaki Yaegashi, Kanagawa (JP); Shoko Kano, Kanagawa (JP); Masahiko Yamanaka, Kanagawa (JP); Kentarou Watanabe, Kanagawa (JP); Hiroshi Yokoyama, Kanagawa (JP); Hideo Sawada, Aomori (JP)

(73) Assignee: Nissan Motor Co., Ltd., Yokohama-shi (JP)

( * ) Notice: Subject to any disclaimer, the term of this patent is extended or adjusted under 35 U.S.C. 154(b) by 1104 days.

(21) Appl. No.: 11/715,495

(22) Filed: Mar. 8, 2007

(65) Prior Publication Data
US 2008/0064903 A1 Mar. 13, 2008

(30) Foreign Application Priority Data
Sep. 13, 2006 (JP) ................... 2006-248066

(51) Int. Cl.
*C07C 27/10* (2006.01)
(52) U.S. Cl. ...................................... 568/700
(58) Field of Classification Search .................. None
See application file for complete search history.

(56) References Cited

U.S. PATENT DOCUMENTS
6,558,455 B2 * 5/2003 Sammons et al. .................. 96/4

OTHER PUBLICATIONS

H. Sawada et al., "Solubilization of fullerene into ionic liquids by the use of fluoroalkyl end-capped oligomers," Polymers for Advanced Technologies, vol. 16, 2005, pp. 655-658.

H. Sawada et al., "Solubilization of fullerene into water with fluoroalkyl end-capped amphiphilic oligomers—novel fluorescence properties," Journal of Colloidal and Interface Science 263 (2003), pp. 1-3.

H. Sawada, "Construction of Nano-level Structure-controlled Fluorine-based Molecule Aggregate and Coating Surface Improvement," Science Council of Japan, 11$^{th}$ Interface Symposium, (2004), pp. 63-85.

U.S. Appl. No. 11/715,496, filed Mar. 8, 2007, Yaegashi et al.

* cited by examiner

*Primary Examiner* — Shawquia Young
(74) *Attorney, Agent, or Firm* — Foley & Lardner LLP

(57) ABSTRACT

A nanoparticle composite includes a host molecule including a chain oligomer section having a hydrophilic group and fluoroalkyl groups respectively at opposite terminals thereof and a three-dimensional silica network section, and having a structure represented by the following formula (1):

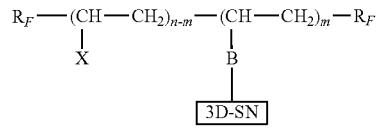

where X is the hydrophilic group and is independent OH group, independent NCO group, independent $NH_2$ group, independent NHR group (where R is alkyl group) or independent OCY group (where Y is a hydrophilic group); $R_F$ is the fluoroalkyl group having a carbon number of 2 to 10 and a molecular weight of 119 to 1000; 3D-SN is the three-dimensional silica network section; B is independent O, independent O=C=O, independent NH—C=O or independent NR—C=O (where R is alkyl group); n is $1 \leq n \leq 10$; and m is $1 \leq m \leq n$; and a guest molecule included in the host molecule.

4 Claims, No Drawings

NANOPARTICLE COMPOSITE

BACKGROUND OF THE INVENTION

This invention relates to a nanoparticle composite, and more particularly to a nanoparticle composite which can be used when a fine guest molecule is dispersed and dissolved in an aqueous solution, an organic solvent, a resinous medium or the like.

An oligomer having fluoroalkyl groups respectively at its opposite terminals and having hydrophilic groups in its main chain forms a molecule aggregate under a self-organization. Additionally, this molecule aggregate provides a host field for fullerene and has such a property as to cause fullerene to serve as guest molecule.

In this connection, such a molecule aggregate has an amphipathic property, and therefore it is known that the molecule aggregate has the performance of serving as a dispersion assistant for fullerene which is slightly soluble and low dispersible in water and organic solvents (See, for example, Non-patent literatures 1 to 3).

[Non-patent literature 1] H. Sawada, R. Kasai et al., polym. Adv. Tech., 16, 655 (2005);

[Non-patent literature 2] H. Sawada, J. Iidzuka et al., J. Colloid Interface Sci., 263, 1 (2003); and

[Non-patent literature 3] Hideo Sawada et al., 11$^{th}$ Interface Symposium Lecture Preliminary Reports for Science Council of Japan, 2004, Pages 63 to 85.

SUMMARY OF THE INVENTION

However, the above-mentioned molecule aggregate has encountered the following problem: In case that solutes other than fullerene exists in a solvent, the molecule aggregate takes them in as guest molecules. Accordingly, dispersion of fullerene as an object cannot be accomplished as being intended, so that a stable dispersion cannot be made.

An object of the present invention is to provide an improved nanoparticle composite which can effectively solve the problem encountered by conventional techniques.

Another object of the present invention is to provide an improved nanoparticle composite which can stably disperse a solute molecule as an object even in a solvent containing plural kinds of solute molecules for which a stable dispersion cannot be conventionally accomplished.

In order to solve the above-mentioned problem, the present inventors have eagerly made many studies. As a result, they have found that the above-mentioned problem can be solved by combining a chain oligomer section having fluoroalkyl group and a three-dimensional silica network section to form a certain structure, thus reaching the completion of the present invention.

In other words, a nanoparticle composite according to the present invention comprises a host molecule including a chain oligomer section having a hydrophilic group and fluoroalkyl groups respectively at opposite terminals thereof and a three-dimensional silica network section, and having a structure represented by the following formula (1):

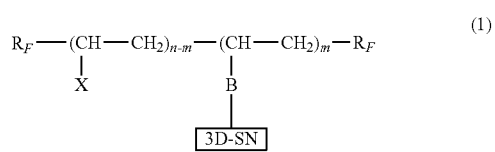

where X is the hydrophilic group and is independent OH group, independent NCO group, independent NH$_2$ group, independent NHR group (where R is alkyl group) or independent OCY group (where Y is a hydrophilic group); R$_F$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); n is $1 \leq n \leq 10$; and m is $1 \leq m \leq n$; and a guest molecule included in the host molecule.

Additionally, in a preferable embodiment of the nanoparticle composite according to the present invention, the molecular weight of the chain oligomer section in the above-mentioned formula (1) is 252 to 100,000.

DETAILED DESCRIPTION OF THE INVENTION

Hereinafter, the nanoparticle composite according to the present invention will be discussed further in detail. In the specification and the claims of the present application, "%" for concentration, content, filling amount or the like represents % by mass unless otherwise specified.

A nanoparticle composite according to the present invention comprises a host molecule including a chain oligomer section having a hydrophilic group and fluoroalkyl groups respectively at opposite terminals thereof and a three-dimensional silica network section (3D-SN), and having a structure represented by the following formula (1):

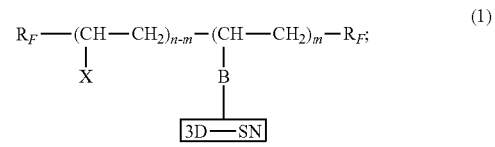

and a guest molecule included in the host molecule. It is to be noted that n is $1 \leq n \leq 10$, and m is $1 \leq m \leq n$.

Here, in the above-mentioned formula (1), X is a hydrophilic group which is selected from independent hydroxyl group (OH group), independent isocyanate group (NCO group), independent amino group (NH$_2$) group, independent imino group (NHR group where R is alkyl group), independent OCY group (where Y is a hydrophilic group) which is represented by the following chemical formula:

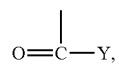

or any combination of the above-listed hydrophilic groups.

Additionally, the hydrophilic group of the above-mentioned OCY group is not particularly limited and is suitably selected from, for example, functional groups (hydroxyl group, morpholine group, N-(1,1-dimethyl-3-oxobutyl) amino group and dimethylamino group) which are respectively independent and shown below, sulfone group and amino group other than the above-mentioned. It is to be noted that Y may not of the same kind in the same oligomer molecule.

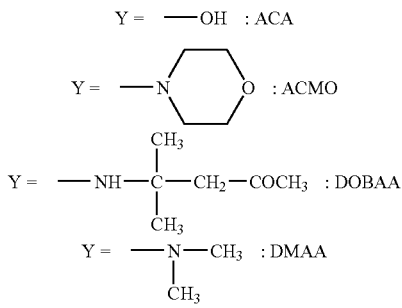

Additionally, a linkage section (B) between the chain oligomer section and the three-dimensional silica network section is originated from the above-mentioned hydrophilic group. Examples of the linkage section are the following structures independent from each other: ether linkage (O), ester linkage (O=C—O), amide linkage (NH—C=O or NR—C=O where R is alkyl group) and the like.

Further, fluoroalkyl group (RF) has a carbon number of 2 to 10 and a molecular weight of 119 to 1000.

In other words, perfluoroalkyl group ($C_nF_{2n+1}$ where $2 \leq n \leq 10$) or a functional group in which perfluoroalkyl group have some ether linkages can be used, in which it is sufficient that the total molecular weight is 119 to 1000. Additionally, the above-mentioned fluoroalkyl group may be of a configuration including C, F, H or O.

Furthermore, as the three-dimensional silica network section (3D-SN), the three-dimensional network structure represented by the following chemical formula is exemplified in the form of a typical schematic illustration:

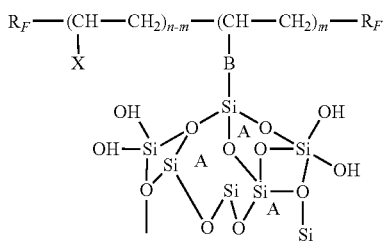

In concrete, the above configuration can be obtained by using colloidal silica having particle sizes of 1 to 500 nm.

Thus, the nanoparticle composite according to the present invention has such a structure that the three-dimensional silica network section (3D-SN) having the three-dimensional network structure with siloxane linkages [(—Si—O—)n] serves as a nuclear, and the chain oligomer section having hydrophilic group (X) and fluoroalkyl groups ($R_F$) at the opposite terminals thereof exist extending along the proximity of the outer peripheral portion of the three-dimensional silica network section. Accordingly, the guest molecule can be directly introduced into the host molecule, so that the guest molecule as an object can be stably dispersed by controlling the size of the chain oligomer section and the silica network section even in a solvent containing particles other than the guest molecule which cannot be stably dispersed in conventional techniques.

The following two reasons are assumed for this:

1) In the conventional techniques, guest molecule is trapped under van der Waals force. In contrast, according to the present invention, guest molecule as the object can be securely trapped by being physically confined in the three-dimensional network structure with siloxane linkages [(—Si—O—)n], not only under van der Waals force.

2) Since the nanoparticle composite of the present invention makes its aggregation, and therefore the number of fluoroalkyl groups per unit area increases so that a function as an emulsifier (surface active agent) is improved.

Additionally, a plurality of the nanoparticle compositees of the present invention aggregate to form a structure represented by the following formula (3):

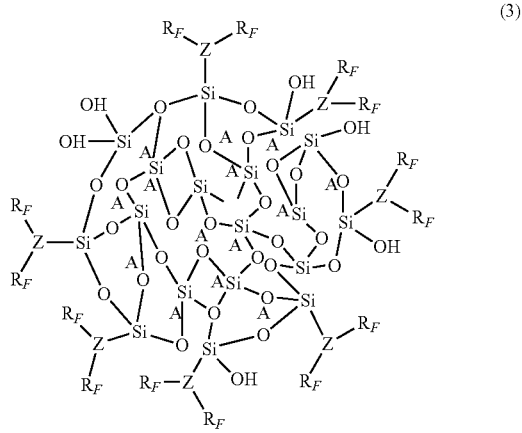

(3)

In this case, the chain oligomer section is represented by $(RF)_2>Z-$ and preferably has a total molecular weight of 252 to 100,000.

Examples of Z are, for example, ones represented by the following chemical formulae:

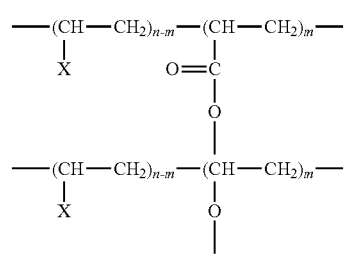

Further, from the viewpoint of improving the function of confining the guest molecule in the aggregate of the three-dimensional silica network sections, it is preferable to use tetraethoxysilane (TEOS) during production.

By this, the functional groups (functional groups including the terminal fluoroalkyl groups and the hydrophilic group) to be provided to the surface of the three-dimensional silica network section can be effectively taken in the nanoparticle composite.

In the nanoparticle composite according to the present invention, the guest molecule (A) is not particularly limited if it is fine particle having a size of about 0.5 to 500 nm. Examples of the guest molecule are carbon nanotube, carbon nanohorn, HIV virus, fullerene, magnetic particle (magnetite particle), gold particle, silver particle, nanodiamond particle, hibitane, fluorescein and the like. Further, by-product carbon particle in production of fullerene, known as a functional material can be also used as the guest molecule.

These can be included in the three-dimensional network structure of the siloxane linkages [(—Si—O—)n] included in the three-dimensional silica network section.

The "nanoparticle composite" in the specification and claims of the present application means typically a particle or composite of the nano-order in size; however, it may not be of the nano-order and therefore includes ones having particle sizes of about 0.5 nm to about 1 μm.

The above-mentioned fullerene is not limited to one of C60 and therefore may be higher order fullerenes, for example, ones of C70, C74, C76, C78, C78, C80, C82 . . . . (These fullerenes follow "isolated five-ring rule").

The above-mentioned by-product carbon particle in production of fullerene means by-product carbon particle produced in a fullerene production method which is called a combustion method and a carbon material having any one of the following properties (1) to (5):

(1) A carbon material which is insoluble in organic solvents, and has an angle of diffraction within a range of from 3 to 30° in result of an X-ray diffraction using CuKα ray, in which the most intensive peak exists within a range of 10 to 18° in angle of diffraction.

(2) A carbon material which has such a property of being insoluble in organic solvents that a weight reduction of the carbon material is not more than 5% upon being subjected to a vacuum drying at 150° C. for 10 hours after 1,2,4-trimethylbenzene in an amount of 90 times by weight of the carbon material is added to the carbon material and then stirred and filtered.

(3) A carbon material which has peaks at a band G 1590±20 $cm^{-1}$ and a band D 1340±40 $cm^{-1}$ in result of a Raman spectrum at an excitation wavelength of 5145 A, in which a peak intensity ratio I(D)/I(G) is within a range of 0.4 to 1.0 where peak intensities of the bands G, D are respectively I(G) and I(D).

(4) A carbon material whose peak does not exist at an angle of diffraction of 23 to 27°.

(5) A carbon material which is not less than 10 $m^2/g$ and less than 200 $m^2/g$ in specific surface area measured by a nitrogen adsorption method and less than 10% in rate of volume of pores of not larger than 10 A relative to volume of pores of not larger than 300 A.

Additionally, in the nanoparticle composite according to the present invention, the guest molecule (A) can be introduced in the chain oligomer section.

In concrete, the guest molecule can be contained in at least one of sections A1 to A3 indicated in the following formula (2):

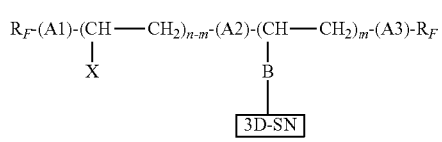

(where n is 1≦n≦10; and m is 1≦m≦n.)

It is to be noted that it is sufficient that the guest molecule is introduced into at least one CH—CH$_2$ linkage in (CH-(A2)-CH$_2$)$_n$ in the formula (2).

Next, an embodiment of production method of the above-mentioned nanoparticle composite will be discussed.

1. Production Method of Chain Oligomer (1-1) Production of Perfluoroacyl Chloride Anhydrous perfluorocarboxylic acid ($R_FCO_2H$) and benzoil chloride (PhCOCl) were mixed in a rate of 1:2 mmol and then rapidly heated at the boiling point of the anhydrous perfluorocarboxylic acid or a temperature slightly higher than the boiling point and cooled to a room temperature.

The obtained crude product was subjected to a fractional distillation to be purified thereby obtaining perfluoroacyl chloride ($R_FCOCl$).

For example, in case that $CF_3CF_2CF_2CO_2H$ is used as anhydrous perfluorocarboxylic acid ($R_FCO_2H$), the yield of $CF_3CF_2CF_2COCl$ is 70%; in case that the yield of $CF_3CF_2CF_2CF_2CF_2CF_2CF_2CO_2H$ is used as anhydrous perfluorocarboxylic acid, the yield of $CF_3CF_2CF_2CF_2CF_2CF_2CF_2COCl$ is 77%; in case that $HCF_2CF_2CO_2H$ is used as anhydrous perfluorocarboxylic acid, the yield of $HCF_2CF_2COCl$ is 71%; in case that $HCF_2CF_2CF_2CF_2CO_2H$ is used as anhydrous perfluorocarboxylic acid, the yield of $HCF_2CF_2CF_2CF_2COCl$ is 70%, thus obtaining the perfluoroacyl chloride as an object.

(1-2) Production of Fluoroalkanoyl Peroxide

Perfluoroacyl chloride ($R_FCOCl$), NaOH and $H_2O_2$ are contained at mol ratio of 1:1:0.5 in a sufficient amount of a nonpolar fluorine solvent (Freon-113: $CF_2ClCFCl_2$) which is kept at −5° C. to −7° C. For this, first a sodium hydroxide aqueous solution prepared by dissolving NaOH at a rate of 0.12 g per 1 ml of water; subsequently a 30% hydrogen peroxide aqueous solution is added and a quick stirring is made; and thereafter $R_FCOCl$ which has been previously cooled at −5° C. to −7° C. is added and then stirring is made for 2 minutes.

Thereafter, the temperature is slightly raised (however, to not higher than 0° C.), and then allowing to stand is made after stirring for 6 to 7 minutes is made. Then, an oily layer is extracted from two separate oily and aqueous layers thereby obtaining fluoroalkanoyl peroxide (($R_FCOO)_2$) as an objective product.

It is to be noted that it is preferable to rinse the product with a saturated sodium hydrogencarbonate which has been cooled by ice.

Additionally, perfluoroacyl chloride used for fluoroalkanoyl peroxide may be replaced with a halide compound such as perfluoroacyl fluoride, perfluoroacyl bromide or the like.

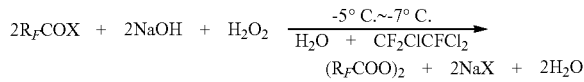

where $R_F$: fluoroalkyl group,
X: halogen (1-3) Production of Oligomer Having Fluoroalkyl Groups Respectively at its Opposite Terminals and Hydrophilic Group in its Main Chain Fluoroalkanoyl peroxide, for example, perfluoro-2-methyl-3-oxahexanoyl peroxide in an amount of 5 mmol is added to 35 g of a fluorine-based solvent (AK-225 which is a mixture solvent (1:1) of 1,1-dichloro-2,2,3,3,3-pentafluoropropane and 1,3-dichloro-1,2,2,3,3-pentapentafluoropropane). To this solution, a mixture solution of 24 mmol of a monomer having hydrophilic group, for example, acryloyl-morpholine (ACMO) and 50 g of the fluorine-based solvent (AK-225) is added, and then stirring is made at 45° C. for 5 hours in a nitrogen atmosphere.

After the stirring, the solvent is evaporated thereby obtaining 4.55 g of bis(perfluoro-1-methyl-2-oxapentylated) ACMO oligomer.

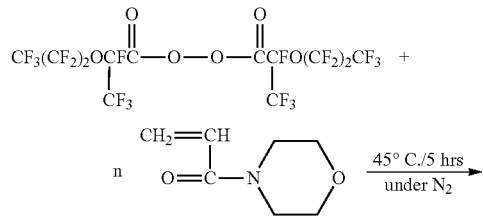

Additionally, as the oligomer having the fluoroalkyl groups respectively at its opposite terminals and the hydrophilic group in its main chain, the following compounds other than the above-mentioned ones may be used as fluoroalkanoyl peroxide: $(CF_3CF_2CF_2COO)_2$, $(CF_3CF_2CF_2CF_2CF_2CF_2COO)_2$, $(HCF_2CF_2COO)_2$, $(HCF_2CF_2CF_2CF_2COO)_2$, $(HCF_2CF_2CF_2CF_2CF_2COO)_2$, $(C_3F_7OCF(CF_3)CF_2OCF(CF_3)COO)_2$, $(C_3F_7OCF(CF_3)COO)_2$, and the like.

As the monomer having the hydrophilic group, for example, N,N-dimethylacrylamide (DMAA), acrylic acid (ACA), N-(1,1-dimethyl-3-oxoisobutyl) acrylamide (DOBAA) and the like other than the above-mentioned ones may be used.

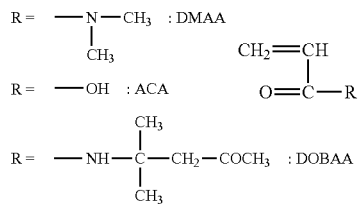

2. Production Method of Other Chain Oligomer Section (Co-Oligomer Including Guest Molecule in its Main Chain)

Fluoroalkanoyl peroxide, for example, perfluoro-2-methyl-3-oxahexanoyl peroxide in an amount of 5 mmol is added to 35 g of fluorine-based solvent (AK-225 which is a mixture solvent (1:1) of 1,1-dichloro-2,2,3,3,3-pentafluoropropane and 1,3-dichloro-1,2,2,3,3-pentapentafluoropropane) to prepare a solution. To this solution, a mixture solution of 24 mmol of monomer having hydrophilic group, for example, acryloylmorpholine (ACMO) and 50 g of the fluorine-based solvent (AK-225) is added, and then 0.6 mmol of fullerene is added as guest molecule, followed by making stirring at 45° C. for 5 hours in a nitrogen atmosphere. After the stirring, the solvent is evaporated thereby obtaining fullerene co-oligomer in a yield of 60%.

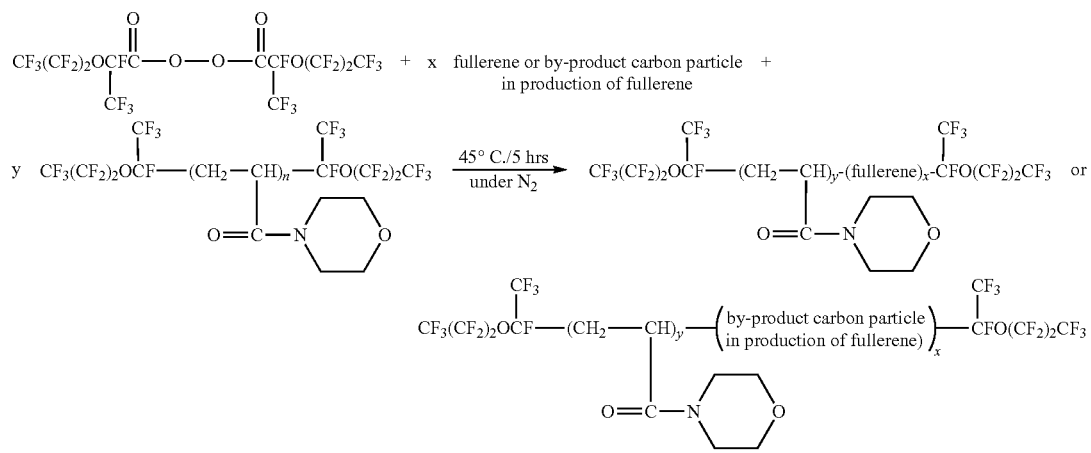

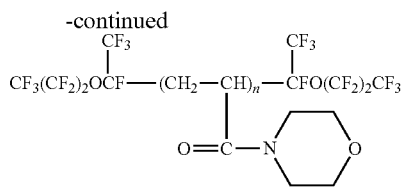

It is to be noted that, concerning the above fullerene co-oligomer, the co-oligomer can be produced with carbon compound other than fullerene, more specifically the above-mentioned by-product carbon particle in production of fullerene, in similar production methods. Additionally, concerning the hydrophilic group, limitation is hot made to ACMO similarly to in the above-mentioned oligomer.

3. Production Method of Nanoparticle Composite

An oligomer having fluoroalkyl groups respectively at its opposite terminals, for example, bis(perfluoro-1-methyl-2-oxapentylated) DOBAA oligomer in an amount of 6 g is dissolved in 500 ml of tetrahydrafuran (=THF). Then, 0.6 g of fullerene is further added, and a solubilization is made for two weeks.

The obtained solution, 40 g of methanol silica sol (silica sol containing 70% of methanol, in which silica particle has an average particle size of about 10 nm), 6 g of TEOS and 6 ml of 25% aqueous ammonia are subjected to reaction for 3 hours.

After the reaction, the solvent is removed upon evaporation, thereby making it possible to obtain the nanoparticle composite in a yield of not lower than 80%.

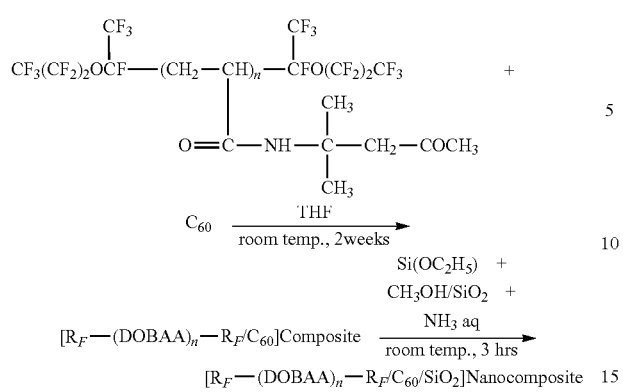

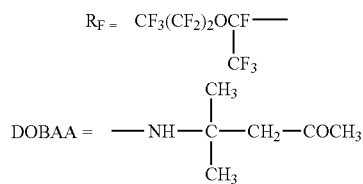

It is to be noted that the structures of $R_F$ and DOBAA in the above-mentioned reactions will be shown in the following:

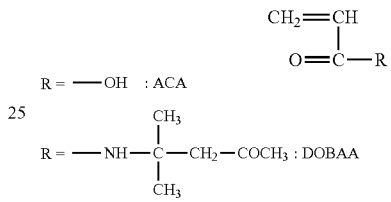

The above-mentioned nanoparticle composite can be produced with carbon compound other than fullerene, more specifically, the by-product carbon particle in production of fullerene, in a similar production method.

EXAMPLES

Hereinafter, the present invention will be discussed further in detail with reference to Examples and Comparative Examples; however, the present invention is not limited to these Examples.

Examples 1 to 19 and Comparative Examples 1 to 22

In each Example or Comparative Example, the nanoparticle composite was produced according to the above-discussed production method.

Additionally, the chain oligomer section, the three-dimensional silica network section and the guest molecule were used upon being selected from materials shown below.

Details are shown in Table 1.

1. The Chain Oligomer Section Having Hydrophilic Group and Fluoroalkyl Groups Respectively at its Opposite Terminals
   (1) $R_F$-(ACA)$_n$-RF
   (2) $R_F$-(DOBAA)$_n$-RF
   (3) $R_F$-(fullerenes)$_x$-(ACA)$_y$-$R_F$
   (4) $R_F$-(fullerenes)$_x$-(DOBAA)$_y$-$R_F$ It is to be noted that HFPO2 represented by the following chemical formula was used for the above-mentioned $R_F$.

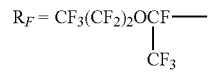

The above-mentioned ACA and the above-mentioned DOBAA are represented by the following chemical formula:

$$CH_2{=}CH$$
$$O{=}C{-}R$$

$R = $ —OH : ACA $R = $ —NH—C(CH$_3$)(CH$_3$)—CH$_2$—COCH$_3$ : DOBAA

Concerning the above-mentioned fullerenes, C60 was used as fullerenes (1); a mixture C60/C70 (nanom mix: produced by Frontier Carbon Corporation) was used as fullerenes (2); and by-product carbon particle in production of fullerene (nanom black: produced by Frontier Carbon Corporation) was used as fullerenes (3).

2. The Three-Dimensional Silica Network Section

Colloidal silica ($SiO_2$) having an average particle size of 10 nm was used.

3. The Guest Molecule

C60 was used as fullerenes (1); a mixture C60/C70 (nanom mix: produced by Frontier Carbon Corporation) was used as fullerenes (2); and by-product carbon particle in production of fullerene (nanom black: produced by Frontier Carbon Corporation) was used as fullerenes (3).

(Evaluation Test)

The nanoparticle composite obtained in each Example and Comparative Example in an amount of 1 g was prepared and added in 100 ml of each solvent ($H_2O$, MeOH, EtOH, THF, Hexane), upon which the degree of dispersion and solubility was evaluated by a visual observation. The results of this test are shown in Table 1.

TABLE 1

|  |  |  | $H_2O$ | MeOH | EtOH | THF | Hexane |
|---|---|---|---|---|---|---|---|
| Example | 1 | [RF-(ACA)$_n$-RF/fullerenes(1)/SiO$_2$]Nanocomposite | ⊚ | ○ | ○ | ⊚ | X |
|  | 2 | [RF-(ACA)$_n$-RF/fullerenes(2)/SiO$_2$]Nanocomposite | ⊚ | ○ | ○ | ⊚ | X |
|  | 3 | [RF-(ACA)$_n$-RF/fullerenes(3)/SiO$_2$]Nanocomposite | ⊚ | ○ | ○ | ⊚ | X |
|  | 4 | [RF-(DOBAA)$_n$-RF/fullerenes(1)/SiO$_2$]Nanocomposite | X | ○ | ○ | ⊚ | Δ |
|  | 5 | [RF-(DOBAA)$_n$-RF/fullerenes(2)/SiO$_2$]Nanocomposite | X | ○ | ○ | ⊚ | Δ |
|  | 6 | [RF-(DOBAA)$_n$-RF/fullerenes(3)/SiO$_2$]Nanocomposite | X | ○ | ○ | ⊚ | Δ |
|  | 7 | [RF-(fullerenes(1))$_x$-(ACA)$_y$-RF/fullerenes(1)/SiO$_2$]Nanocomposite | ⊚ | ○ | ○ | ⊚ | X |
|  | 8 | [RF-(fullerenes(1))$_x$-(ACA)$_y$-RF/fullerenes(2)/SiO$_2$]Nanocomposite | ⊚ | ○ | ○ | ⊚ | X |
|  | 9 | [RF-(fullerenes(1))$_x$-(ACA)$_y$-RF/fullerenes(3)/SiO$_2$]Nanocomposite | ⊚ | ○ | ○ | ⊚ | X |
|  | 10 | [RF-(fullerenes(2))$_x$-(ACA)$_y$-RF/fullerenes(1)/SiO$_2$]Nanocomposite | ⊚ | ○ | ○ | ⊚ | X |
|  | 11 | [RF-(fullerenes(2))$_x$-(ACA)$_y$-RF/fullerenes(2)/SiO$_2$]Nanocomposite | ⊚ | ○ | ○ | ⊚ | X |
|  | 12 | [RF-(fullerenes(2))$_x$-(ACA)$_y$-RF/fullerenes(3)/SiO$_2$]Nanocomposite | ⊚ | ○ | ○ | ⊚ | X |
|  | 13 | [RF-(fullerenes(3))$_x$-(ACA)$_y$-RF/fullerenes(1)/SiO$_2$]Nanocomposite | ⊚ | ○ | ○ | ⊚ | X |

TABLE 1-continued

|  |  |  | $H_2O$ | MeOH | EtOH | THF | Hexane |
|---|---|---|---|---|---|---|---|
| | 14 | [RF-(fullerenes(3))$_x$-(ACA)$_y$-RF/fullerenes(2)/SiO$_2$]Nanocomposite | ⊚ | ○ | ○ | ⊚ | X |
| | 15 | [RF-(fullerenes(3))$_x$-(ACA)$_y$-RF/fullerenes(3)/SiO$_2$]Nanocomposite | ⊚ | ○ | ○ | ⊚ | X |
| | 16 | [RF-(fullerenes(1))$_x$-(DOBAA)$_y$-RF/fullerenes(1)/SiO$_2$]Nanocomposite | X | ○ | ○ | ⊚ | Δ |
| | 17 | [RF-(fullerenes(2))$_x$-(DOBAA)$_y$-RF/fullerenes(2)/SiO$_2$]Nanocomposite | X | ○ | ○ | ⊚ | Δ |
| | 18 | [RF-(fullerenes(2))$_x$-(DOBAA)$_y$-RF/fullerenes(3)/SiO$_2$]Nanocomposite | X | ○ | ○ | ⊚ | Δ |
| | 19 | [RF-(fullerenes(3))$_x$-(DOBAA)$_y$-RF/fullerenes(3)/SiO$_2$]Nanocomposite | X | ○ | ○ | ⊚ | Δ |
| Comparative Example | 1 | fullerenes(1)(=C60)single | X | X | X | X | X |
| | 2 | fullerenes(2)(=C60/C70 mixture)single | X | X | X | X | X |
| | 3 | fullerenes(3)(=by-product carbon particle in production of fullerene)single | X | X | X | X | X |
| | 4 | [RF-(ACA)$_n$-RF/fullerenes(1)/SiO$_2$]Composite | ○ | Δ | Δ | Δ | X |
| | 5 | [RF-(ACA)$_n$-RF/fullerenes(2)/SiO$_2$]Composite | Δ | Δ | Δ | Δ | X |
| | 6 | [RF-(ACA)$_n$-RF/fullerenes(3)/SiO$_2$]Composite | ○ | Δ | Δ | Δ | X |
| | 7 | [RF-(DOBAA)$_n$-RF/fullerenes(1)/SiO$_2$]Composite | X | Δ | Δ | ▲ | X |
| | 8 | [RF-(DOBAA)$_n$-RF/fullerenes(2)/SiO$_2$]Composite | X | Δ | Δ | Δ | X |
| | 9 | [RF-(DOBAA)$_n$-RF/fullerenes(3)/SiO$_2$]Composite | X | Δ | Δ | ▲ | X |
| | 10 | [RF-(fullerenes(1))$_x$-(ACA)$_y$-RF/fullerenes(1)/SiO$_2$]Composite | ⊚ | Δ | Δ | Δ | X |
| | 11 | [RF-(fullerenes(1))$_x$-(ACA)$_y$-RF/fullerenes(2)/SiO$_2$]Composite | Δ | Δ | Δ | Δ | X |
| | 12 | [RF-(fullerenes(1))$_x$-(ACA)$_y$-RF/fullerenes(3)/SiO$_2$]Composite | ⊚ | Δ | Δ | Δ | X |
| | 13 | [RF-(fullerenes(2))$_x$-(ACA)$_y$-RF/fullerenes(1)/SiO$_2$]Composite | Δ | Δ | Δ | Δ | X |
| | 14 | [RF-(fullerenes(2))$_x$-(ACA)$_y$-RF/fullerenes(2)/SiO$_2$]Composite | ○ | Δ | Δ | Δ | X |
| | 15 | [RF-(fullerenes(2))$_x$-(ACA)$_y$-RF/fullerenes(3)/SiO$_2$]Composite | ○ | Δ | Δ | Δ | X |
| | 16 | [RF-(fullerenes(3))$_x$-(ACA)$_y$-RF/fullerenes(1)/SiO$_2$]Composite | ○ | Δ | Δ | Δ | X |
| | 17 | [RF-(fullerenes(3))$_x$-(ACA)$_y$-RF/fullerenes(2)/SiO$_2$]Composite | Δ | Δ | Δ | Δ | X |
| | 18 | [RF-(fullerenes(3))$_x$-(ACA)$_y$-RF/fullerenes(3)/SiO$_2$]Composite | ○ | Δ | Δ | Δ | X |
| | 19 | [RF-(fullerenes(1))$_x$-(DOBAA)$_y$-RF/fullerenes(1)/SiO$_2$]Composite | X | Δ | Δ | Δ | X |
| | 20 | [RF-(fullerenes(2))$_x$-(DOBAA)$_y$-RF/fullerenes(2)/SiO$_2$]Composite | X | Δ | Δ | ○ | X |
| | 21 | [RF-(fullerenes(3))$_x$-(DOBAA)$_y$-RF/fullerenes(3)/SiO$_2$]Composite | X | Δ | Δ | Δ | X |

Solubility: X, ▲, Δ, ○, ⊚
Bad ←→ Good

Table 1 reveals that the nanoparticle composites of Examples as the preferred embodiments of the present invention are good in dispersion and solubility in THF, methanol and ethanol, and excellent in hydrophilic property and lipophilic property.

As apparent from the above, according to the present invention, a certain structure is formed by combining the chain oligomer section having fluoroalkyl group and the three-dimensional silica network, thereby providing the nanoparticle composite which makes it possible to stably disperse objective solute molecule even in a solvent containing plural kinds of solute molecules for which a stable dispersion has not been possible.

The entire contents of Japanese Patent Application No. 2006-248066, filed Sep. 13, 2006, are incorporated herein by reference.

Although the invention has been described above by reference to certain embodiments and examples of the invention, the invention is not limited to the embodiments and examples described above. Modifications and variations of the embodiments and examples described above will occur to those skilled in the art, in light of the above teachings. The scope of the invention is defined with reference to the following claims.

INDUSTRIAL USABILITY

The nanoparticle composite according to the present invention causes guest molecule to be dispersed in any media thereby making it possible to improve the function of the media.

For example, it is considered to be applied to, for example, paints, rubber products (tires and the like), cosmetics, cells, resinous products (household electrical appliances, automotive parts, sporting goods (tennis rackets, golf clubs and the like)).

What is claimed is:

1. A nanoparticle composite comprising:
a host molecule including a chain oligomer section having a hydrophilic group and fluoroalkyl groups respectively at opposite terminals thereof and a three-dimensional silica network section, and the host molecule having a structure represented by the following formula (1):

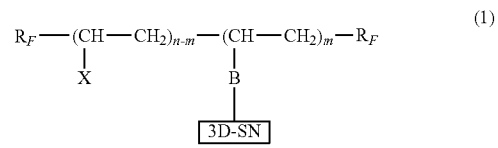

where X is the hydrophilic group and is selected from the group consisting of an OH group, an NCO group, an NH$_2$ group, an NHR group (where R is alkyl group) and an OCY group (where Y is a hydrophilic group); R$_F$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); n is 1≦n≦10; and m is 1≦m≦n; and
a guest molecule which is trapped by being confined in the three-dimensional structure of the host molecule.

2. A nanoparticle composite as claimed in claim 1, wherein the chain oligomer has a molecular weight of 252 to 100,000.

3. A nanoparticle composite comprising:
a host molecule including a chain oligomer section having a hydrophilic group and fluoroalkyl groups respectively at opposite terminals thereof and a three-dimensional silica network section,
the nanoparticle composite having a structure represented by the following formula (2):

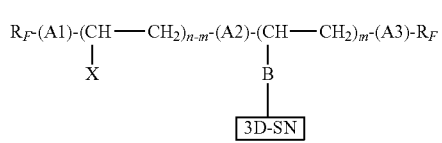 (2)

where X is the hydrophilic group and is selected from the group consisting of an OH group, an NCO group, an $NH_2$ group, an NHR group (where R is alkyl group) and an OCY group (where Y is a hydrophilic group); $R_F$ is the fluoroalkyl group having a carbon number of 2 to 10 and a molecular weight of 119 to 1000; 3D-SN is the three-dimensional silica network section; B is independent O, independent O=C—O, independent NH—C=O or independent NR—C=O (where R is alkyl group); n is $1 \leq n \leq 10$; and m is $1 \leq m \leq n$; and a guest molecule which is trapped by being confined in the three-dimensional structure of the host molecule, wherein the guest molecule is included in at least one of sections represented as A1 to A3 (where $1 \leq n \leq 10$, and $1 \leq m \leq n$).

4. A nanoparticle composite as claimed in claim 3, wherein the chain oligomer has a molecular weight of 252 to 100,000.

* * * * *